United States Patent [19]

Poirier et al.

[11] 4,085,112
[45] Apr. 18, 1978

[54] 2-FORMYL-3-ALKYL-BENZOTHIAZOLIUM HALIDE OXIME

[75] Inventors: Robert H. Poirier, Columbus, Ohio; Edward J. Poziomek, Edgewood, Md.

[73] Assignee: The United States of America as represented by the Secretary of the Army, Washington, D.C.

[21] Appl. No.: 223,310

[22] Filed: Sep. 11, 1962

[51] Int. Cl.² .............................. C07D 275/04
[52] U.S. Cl. ..................... 260/304 C; 252/408
[58] Field of Search ............. 260/302, 304; 252/408, 252/304 C

[56] References Cited

U.S. PATENT DOCUMENTS 3,262,940   7/1966   McElroy et al. ............... 252/408 X Primary Examiner—Leland A. Sebastian
Attorney, Agent, or Firm—Nathan Edelberg; Robert W. Church

EXEMPLARY CLAIM

1. A compound having the formula:

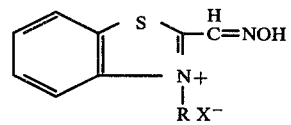

where R is an alkyl group of 1–4 carbons and X is selected from the group consisting of chlorine, bromine, and iodine.

4 Claims, No Drawings

2-FORMYL-3-ALKYL-BENZOTHIAZOLIUM HALIDE OXIME

The invention described herein may be manufactured and used by or for the Government of the U.S. of America for governmental purposes without the payment to us of any royalty thereon.

This invention is directed to new chemical compounds which are useful as colorimetric detectors for phosphorous cholinesterase inhibitors.

Various oximes have been used in the past to detect the "G" agents as is shown by U.S. Pat. Nos. 2,865,719; 2,867,509; 2,926,072; and 2,929,791.

We have discovered a new series of compounds which will react with phosphorus compounds of the type disclosed in U.S. Pat. No. 3,014,943 and British Pat. No. 797,603, to give an almost instantaneous color change from their normal orange color to purple-black.

These compounds have the general formula:

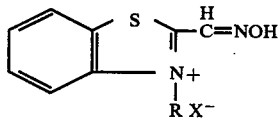

where R is an alkyl group of 1–4 carbons and X is a chlorine, bromine or iodine radical.

The above compounds can be prepared by quaternization of benzothiazole-2-carboxaldoxime with an alkyl halide such as methyl halide, ethyl halide, n-propyl halide or n-butyl halide.

The starting material can be prepared by the method set forth by Borsche and Doeller Ann., 537:53 (1939).

EXAMPLE I

A solution of 2.4 gms (0.0135 mole) of benzothiazole-2-carboxaldoxime in 5 ml. of methyl iodide and 15 ml. of methanol was refluxed for twenty hours. The mixture was concentrated, diluted with ethyl ether, and a salt was isolated by filtration to give 1.3 gms m.p. 189°–190° C. (dec) of orange crystals. The 1.6 gms of unreacted oxime that was recovered by evaporation of the filtrate was again treated with methyl iodide. After six hours of refluxing the methiodide was isolated as before to give an additional .3 gms of the product. The two crystalline fractions were combined, dissolved in 100 ml of methanol-ethanol mixture, treated with activated charcoal, concentrated to 50 ml and allowed to crystallize. In this manner 1.2 gms of orange crystals of 2-formyl-3-methyl-benzothiazolium iodide oxime were obtained.

In a similar manner, the following compounds can be prepared with the use of pressure vessels and higher boiling solvents:

2-formyl-3-methyl-benzothiazolium chloride oxime
2-formyl-3-methyl-benzothiazolium bromide oxime
2-formyl-3-ethyl benzothiazolium iodide oxime
2-formyl-3ethyl-benzothiazolium chloride oxime
2-formyl-3-ethyl-benzothiazolium bromide oxime
2-formyl-3-propyl benzothiazolium iodide oxime
2-formyl-3-n-propyl benzothiazolium bromide oxime
2-formyl-3-n-propyl-benzothiazolium chloride oxime
2-formyl-3-n-butyl-benzothiazolium iodide oxime
2-formyl-3-n-butyl-benzothiazolium bromide oxime
2-formyl-3-n-butyl-benzothiazolium chloride oxime

We claim:

1. A compound having the formula:

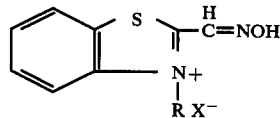

where R is an alkyl group of 1–4 carbons and X is selected from the group consisting of chlorine, bromine, and iodine.

2. 2-Formyl-3-methyl-benzothiazolium iodide oxime.
3. 2-Formyl-3-methyl-benzothiazolium chloride oxime.
4. 2-Formyl-3-methyl-benzothiazolium bromide oxime.

* * * * *